| United States Patent [19] | [11] 4,024,242 |
|---|---|
| Hungerer | [45] May 17, 1977 |

[54] SUBSTANCE HAVING IMMUNOLOGICAL ACTIVITY AND PROCESS FOR ITS MANUFACTURE

[75] Inventor: Klaus-Dieter Hungerer, Marburg-Marbach, Germany

[73] Assignee: Hoechst Aktiengesellschaft, Frankfurt am Main, Germany

[22] Filed: June 23, 1975

[21] Appl. No.: 589,082

[30] Foreign Application Priority Data

June 25, 1974 Germany .......................... 2430380

[52] U.S. Cl. .................................. 424/88; 195/104
[51] Int. Cl.² ...................... A61K 39/00; C12B 1/00
[58] Field of Search ...................... 195/104; 424/88

[56] References Cited

OTHER PUBLICATIONS

Soltys, Chem. Abst., vol. 67 (1967) p. 62560z.
May & Baker, Chem. Abst., vol. 57 (1962) p. 9825b.

*Primary Examiner*—Sam Rosen
*Attorney, Agent, or Firm*—Curtis, Morris & Safford

[57] ABSTRACT

Method of chemically attenuating trypanosomes with a phenanthridine compound, such as 3,8-diamino-5-ethyl-6-phenyl phenanthridine, to obtain non-pathogenic organisms with immunological activity; attenuated organisms produced in this way; vaccines containing such attenuated organisms.

11 Claims, No Drawings

SUBSTANCE HAVING IMMUNOLOGICAL ACTIVITY AND PROCESS FOR ITS MANUFACTURE

The present invention relates to a substance having immunological activity, and to a process for its manufacture by treating living tropanosomes with phenanthridine derivatives for the purpose of suppressing their pathogenicity while fully maintaining their immunological potency. This method, called chemical attenuation, makes it possible to develop a vaccine that may even be administered to human beings.

The invention furthermore relates to a vaccine containing trypanosomes that have been attenuated according to the invention.

Chagas disease is considered one of the great health problems in South and Central America. It is caused by infection with Trypanosoma cruzi. The number of really infected persons living in this subcontinent is being disputed but, in 1960, the World Health Organization (WHO) rated this number of injected at about 7 millions and those exposed to the risk of infection at about 35 millions.

There is a variety of methods used to control this infection; the most important one being perhaps the work on the extirpation of the disease carrier (cone-nosed bugs of the Triatoma species) in the lodgings of the population, health education of the people and sanitation of housing facilities. Supported by WHO, this method is already being carried on with great success in many countries. Another success in the control of the Chagas disease has been the marketing of the chemotherapeutic Lampit(R) (registered trade mark of Farbenfabrik Bayer, Leverkusen, W. Germany), an etiologic agent with a high activity in man. The problem with chemotherapeutics is, however, that the infection brings about irreversible pathological changes, for example in the heart and other hollow organs, which cannot be repaired by administering the medicaments in a relatively late phase of the disease. A prophylactic measure, however, which is generally applied in the treatment of infections of viral or bacterial genesis, i.e. the administration of a vaccine, is still regarded today as involving too many risks.

Although a number of working groups (for example, Kagan, Marsden, Nussenzweig, Menezes, Hungerer) was able to demonstrate that naturally attenuated culture forms of T. cruzi immunize mice that had been injected with them against a lethal infection with pathogenic trypanosomes, the problem still lies with the residual pathogenicity of the culture forms, to be established to a varying extent.

In 1950, J. Emmett reported on a suppression of the pathogenicity of T. cruzi. He exposed still highly infective culture forms to X rays and found out that exposure to 100.000r, though keeping the trypanosomes alive, destroyed their infectivity. These exposed culture forms, however, did no longer immunize mice against a pathogenic infection (Chiari, 1968).

The experiments reported in the disclosure of German Pat. No. 1,234,930 on the chemical modification of trypanosomes (for example, with formalin, hydroxylamine, etc.) also did not lead to a vaccine.

Another method was reported by Fernandes et al. in 1965. They incubated culture and blood forms with actinomycin D. The trypanosomes lost their capacity of multiplication but retained their immonogenic potency. Owing to the high toxicity of Actinomycin D, however, this vaccine cannot be administered to man.

The present invention had to solve the problem of finding an immunologically active substance against the Chagas disease, which substance holds no risk for man because it blocks the residual pathogenicity of culture forms but preserves their full immunological protective effect. The substance used for attentuation should itself be entirely non-toxic for man in the concentration as used in the vaccine. Surprisingly, this substance was found among the class of the phenanthridines.

Phenanthridines were synthetized already in 1938 and tested for their therapeutic efficiency with regard to Trypanosoma congolense and Trypanosoma vivax. In 1946, Browning et al. also showed a chemotherapeutic activity on T. cruzi in mice. This was followed by a number of publications, for example by Riou et al., on the efficiency mechanism of 3,8-diamino-5-ethyl-6-phenylphenanthridinium bromide on T. cruzi.

It has now been found that incubation of trypanosomes with phenanthridine derivatives modifies the vitality and infectivity thereof to such an extent that, after injection with trypanosomes thus treated, mice do not suffer a pathogenic infection but develop full immunization.

Hence, this invention relates to a process for the manufacture of a substance having immunological activity, which comprises incubating trypanosomes that have been suspended in a mono-phase, aqueous culture medium with a phenanthridine derivative until they lose their pathogenicity, and collecting the trypanosomes thus attenuated.

Further objects of this invention are trypanosomes that have been chemically attenuated according to this process, as well as a vaccine containing these.

As phenanthridine derivatives, as understood by this invention, any physiologically acceptable compound of this class is suitable. Especially adequate are derivatives which carry amino groups in the 3-and 8-positions, a pheny radical in the 6-position, and a lower alkyl group in the 5-position, for example 3,8-diamino-5-methyl-6-phenyl-phenanthridine, isometamidine and 3,8-diamino-5-ethyl-6-phenyl-phenanthridine. Since the phenanthridine derivatives are generally sparingly soluble in water, it is recommended to use them in the form of their water-soluble salts according to the invention. As acids for the salt-formation, all organic and especially inorganic acids are suitable inasfar as they have physiologically acceptable anions and form water-soluble salts with phenanthridine derivatives; especially suitable are salts of phenanthridine derivatives with hydrohalic acids, such as hydrochloric acid or hydrobromic acid. Examples of appropriate salts are 3,8-diamino-5-methyl-6-phenyl-phenanthridinium bromide (Dimidiumbromid(R)), isometamidium chloride (Samorin(R)) and, in particular 3,8-diamino-5-ethyl-6-phenyl-phenanthridinium bromide. (Ethidiumbromid(R)).

The phenanthridine derivatives and the salts thereof are used in a concentration which, on the one hand, is sufficiently high to bring about the desired chemical attenuation in trypanosomes and, on the other hand, is not so high as to do lasting damage to the trypanosomes. A concentration ranging from 0.5 to 1000$\gamma$ per ml, preferably from 5 to 100$\gamma$ /ml, has proved to be adequate.

The trypanosomes are advantageously treated according to the invention in a concentration of $10^3$ to $10^8$ trypanosomes per ml, advantageously from 1 to 5 × $10^7$ trypanosomes per ml. In this concentration, the trypanosomes are suspended in a liquid culture medium suitable of fully maintaining the metabolism of these organs. As culture medium, any medium which is appropriate for cultivating trypanosomes is suitable, a criterion being that it contains as few as possible or even no antigen determinants. This condition is fulfilled, above all, by protein-free media. Examples of appropriate culture media are the liver-infusion tryptose medium (LIT, according to Camargo (1964)), furthermore, protein-free, chemically defined media as disclosed, for example by Morgan, Morton and Parker (1950), Salk, Younger and Ward (1954), or Parker, Castor and McCulloch (1957).

The treatment of the trypanosomes suspended in the culture medium with a phenanthridine derivative or a salt thereof takes about 1 to 120, preferably 20 to 48 hours. The temperature ranges from about 18° to 37° C, preferably from 25° to 33° C. In accordance with generally known chemical principles, the period of treatment is the longer, the lower the temperature is. Accordingly, shorter periods of treatment are to be attributed to higher temperatures and vice versa.

After the treatment, the trypanosomes are separated from the culture medium, for example by decanting, filtering or advantageously centrifuging them. If the manufacture of a vaccine is intended, the so-obtained trypanosomes may be again suspended in a physiologically acceptable solution in the concentration suitable for a vaccine.

The experiments described hereinafter are to demonstrate that the trypanosomes treated according to this invention lose their multiplicative power and their pathogenicity and are therefore suitable for the manufacture of a vaccine against the Chagas disease. All the media and equipment used in these experiments have to be handled under strictly sterile conditions.

Evidence for the irreversible stop to multiplication due to the treatment of the invention is, for example, provided in the following manner:

Epimastigot culture forms of T. cruzi, Brazil strain, are cultivated on a diphase blood agar (modified according to Senekjie) fo 4 to 5 days at 28° C. The liquid phase containing the trypanosomes is filtered through sterile gauze. The suspension is centrifuged at a speed of 5,000 G for 20 minutes, and the sediment is washed twice with a physiological sodium chloride solution. The trypanosomes are taken up in a dilute medium according to Parker (1957) to reach a concentration of 2 × $10^7$/ml.

Increasing amounts of 3,8-diamino-5-ethyl-6-phenyl-phenanthridinium bromide (5γ//ml, 10γ /ml, 100γ/ml each) are added to 3 samples each of 2.5 ml. Three samples are treated with Thiocid$^{(R)}$ 1:10.000 which kills the trypanosomes in this concentration while maintaining their outer shape, and three further samples are left untreated. All the samples are incubated for 24 hours at 28° C, then centrifuged at 5,000 G for 20 minutes, and the sediment is taken up in 2.5 ml of the 1:10 dilute medium according to Parker (1957). All the samples are mixed with radioactive $^{14}$C thymidine (0.2 μuC) and incubated for 24 hours at 28° C. Then the trypanosomes are separated by means of a Sartorius filter and washed three times with a physiological sodium chloride solution. The radioactivity of the samples is evaluated quantitatively.

The inhibition of the incorporation of $^{14}$C thymidine in the trypanosomes is a measure for the suppression of the multiplicative power.

TABLE

| Result: | Inhibition of the incorporation of $^{14}$C thymidine |
|---|---|
| Thiocid control | 100% |
| 100 γ/ml of Ethidiumbromid | 100% |
| 10 γ/ml of Ethidiumbromid | 88% |
| 5 γ/ml of Ethidiumbromid | 63% |
| untreated | 0% |

The foregoing Table shows a partial or complete loss of the multiplicative power of the trypanosomes treated according to the invention.

Evidence of the loss of pathogenicity after incubation with 3,8-diamino-5-ethyl-6-phenyl-phenanthridinium bromide may be provided as follows:

A. In heart cell cultures:

30 Hearts taken from non-infected, adult inbred mice (NMRI), each weighing about 20 g, under strictly sterile conditions were taken up in 5 ml of phosphate-buffered sodium chloride solution of pH 7.4 (PBS 7.4) and crushed mechanically, whereupon bleeding and whitish pieces of connective tissue were eliminated. The homogenized heart material was put into a trypsinizing flask and topped up with 20 – 30 ml of PBS 7.4. The suspension was agitated vigorously for a short time by means of a magnetically operated stirrer; after sedimentation for a short time, the supernatent material together with the erythrocytes therein was decanted off, and the residue was stirred for 10 minutes at 35° C while adding 20 ml of a trypsin solution (97 ml of PBS 7.4, 3 ml of 5% sodium bicarbonate, and 0.25% of trypsin). After the mixture had settled for a short time, the supernatent material was separated by decantation. The residue was trypsinized further 6 to 7 times. The decanted supernatant materials were centrifuged (400 × g, for 10 minutes); the sediments were taken up in 75 ml of the following solution, which in the following will be called Dulbeccos medium:

20% of fetal calf's serum

10% of Dulbeccos, Messrs. Biocult Lab., Glasgow,

7% of sodium bicarbonate,

2% of glutamine and 0.5% of penicillin/streptomycin and bi-distilled water to make up 100%.

3 Milliliters each of the suspension of the heart cell tissue were introduced into tubes, so-called Leighton tubes, which were provided with a cover glass, sized 13 × 54 mm. The tubes which had been sealed with a silicone stopper were incubated at 37° C. After 24 hours, a cell monolayer had formed.

From inbred NMRI mice which had been infected subcutaneously with T. cruzi, Brazil strain, about 12 days ago, blood was taken and collected in a citrate buffer solution. This was diluted with Dulbeccos medium to yield a final concentration of 1.5 × $10^6$ trypanosomes per ml. The trypanosome suspension was separated into two halves, one of which was diluted with 3,8-diamino-5-ethyl-6-phenyl-phenanthridinium bromide to 10γ/ml. The two halves were then incubated for 24 hours at 28° C. Then the trypanosomes were separated by centrifuging and taken up in fresh Dulbeccos medium (1.5 × $10^6$/ml).

After the medium had been removed from the cell cultures, 3 ml each of the trypanosome suspension (4.5

$\times 10^6$ in total) were placed into the Leighton tubes and incubated for 72 hours at 33° C. Then the medium was changed and incubation continued for 48 hours.

The cell monolayers on the cover glass placed in the Leighton tubes were then colored according to Giemsa.

Result: Of the cells that had been incubated with untreated trypanosomes, 40 to 70% were infected as shown by the microscopic picture. However, the cells which had been incubated with trypanosomes pretreated with 3,8-diamino-5-ethyl-6-phenyl-phenanthridinium bromide, were not infected.

B. In mice:

Blood was drawn under strictly sterile conditions from NMRI mice which had been infected about 10 days ago with about $5 \times 10^4$ trypanosomes of the Brazil strain per mouse, in the presence of heparin (average concentration $50-200 \times 10^6$/ml). The suspension was diluted with the medium of Parker (1957) to $2 \times 10^6$/ml and divided into two halves. The one half was combined was 3,8-diamino-5-ethyl-6-phenyl-phenanthridinium bromide (final concentration 10γ/ml). The two suspensions were incubated for 24 hours at 37° C. The so-incubated suspensions were subcutaneously administered (0.5 ml per animal = $1 \times 10^6$ trypanosomes per animal) to the mice (12 – 14 g of body weight). The course of the disease was checked by means of the animals' weight, parasitemia and death.

Result:

| Pathogen | Treatment | Weight | Parasitemia | dead animals/ total number |
|---|---|---|---|---|
| T. cruzi | 10γ/ml *) | increasing | 0 to extremely low | 0/10 |
| T. cruzi | — | decreasing | high | 10/10 |

*) 3,8-diamino-5-ethyl-6-phenyl-phenanthridinium bromide

The trypanosomes treated according to the invention have immunizing properties as will be proved in the following:

Evidence of immunization may be provided as follows:

Two groups of mice were inoculated with trypanosomes (epimastigot form). Group A, comprising 10 mice, was given 0.5 ml of culture forms subcutaneously ($5 \times 10^7$ per animal), group B, comprising 10 mice, were given the culture forms treated as in the Example ($5 \times 10^7$ per animal), and group C comprising 10 mice were given 0.5 ml of sodium chloride. After 21 days, all the animals were infected with pathogenic trypanosomes of the Brazil strain ($1 \times 10^5$ per animal, subcutaneously).

Result:

100% of the animals of groups A and B survived for at least 100 days after infection, whilst all the control animals of group C died within 10 to 15 days after infection.

This demonstrates that a parenteral administration of trypanosomes attenuated according to the invention is able to immunize against a lethal infection with trypanosomes.

Hence, still another object of this invention is the manufacture of vaccines effective against the Chagas disease and containing the trypanosomes attenuated according to this invention.

A vaccine containing, as the active ingredient, a suspension of trypanosomes according to the invention in a physiologically acceptable aqueous medium may be prepared in a manner well known to those skilled in the art, preferably while stabilizing the trypanosomes with protective colloids, for example with proteins such as albumin or polysaccharides.

The following Example illustrates the invention.

EXAMPLE:

Treatment of culture forms of T. cruzi with 3,8-diamino-5-ethyl-6-phenyl-phenanthridinium bromide.

All the equipment and media used were handled under strictly sterile conditions.

Starting material was a suspension of T. cruzi in the liquid phase of a blood agar culture medium. The 5-day culture was decanted through sterile gauze into a measuring cylinder, and the concentration of trypanosomes was determined in the starting suspension by means of a Thoma chamber. The count was $25 \times 10^6$ trypanosomes/ml in 75 ml, corresponding to a total amount of $1.8 \cdot 10^9$. The suspension was placed into a 250 ml centrifuging beaker provided with a screw cap (Sorvall USA, Rotor GSA, polycarbonate flasks, plastic sealing cap with 0 rings) and centrifuged for 20 minutes at 4° C in a Sorvall RC-2-B at 4500 r.p.m. (= 3300 xg). The supernatent material was decanted off. The sediment was again suspended in 100 ml of physiological. NaCl and once more centrifuged under the same conditions. The supernatent material was decanted, and the sediment was suspended in a centrifuging beaker in a medium having the following composition:

| Amino acids | ml/l | Vitamins | mg/l |
|---|---|---|---|
| Alanin HCl | 25.0 | Aminobenzoic acid | 0.050 |
| Arginin | 70.0 | Ascorbic acid | 50.000 |
| Aspartic acid | 30.0 | D-Biotin | 0.010 |
| Cystein HCl . H₂O | 260.0 | D-Ca-Pantothenate | 0.010 |
| Cystin | 20.0 | Cholin chloride | 0.500 |
| Glutamic acid | 75.0 | Cocarboxylase | 1.000 |
| Glutamine | 100.0 | Folic acid | 0.010 |
| Glycin | 50.0 | Inosit | 0.500 |
| Histidin HCl . H₂O | 20.0 | Nicotinamide | 0.025 |
| Hydroxyprolin | 10.0 | Nicotinic acid | 0.025 |
| Isoleucin | 20.0 | Pyridoxal HCl | 0.025 |
| Leucin | 60.0 | Pyridoxin HCl | 0.025 |
| Lysin HCl | 70.0 | Riboflavin | 0.010 |
| Methionin | 15.0 | Thiamin HCl | 0.010 |
| Phenylalanin | 25.0 | | |
| Prolin | 40.0 | | |
| Serin | 25.0 | | |
| Threonin | 30.0 | | |
| Tryptophan | 10.0 | | |
| Tyrosin | 40.0 | | |
| Valin | | | |
| furthermore, inorganic salts and other constituents: | | | |
| Tween 80 | 5.0 | Sodium-acetate 3H₂O | 83.0 |
| Cholesterol | 0.2 | Sodium glucuronate | 4.8 |
| Coenzyme A | 2.5 | Thymidin | 10.0 |
| Deoxyadenosin | 10.0 | Triphosphopyridine | |
| Deoxycytidin CHl | 10.0 | -Nucleotide | |
| Deoxyguanosin | 10.0 | -Monosodium | |
| Diphosphopyridine | | -Salt (TPN) | 1.0 |
| -Nucleotide | | Uridin-5'triphosphate | |
| -Tetrahydrate | | -Tetrasodium | |
| -(DPN, 4H₂O) | 7.0 | -Tetrahydrate (UPT) | 1.0 |
| Flavin Adenine | | NaCl | 6800 |
| -Dinucleotide (FAD) | 1.0 | KCl | 400 |
| L-Glutathion | 10.0 | MgSO₄, 7H₂O | 200 |
| | | CaCl₂ (anhyd.) | 200 |
| NaH₂PO₄H₂O | 140 | Glucose | 1000 |
| NaHCO₃ | 2200 | Phenol red | 17 |
| | pH 7.2 | | |

(hereinafter called "medium").

Addition of 85 ml of medium and 5 ml of a solution of 0.9 mg of 3,8-diamino 5-ethyl-6-phenyl-phenanthridinium bromide in medium (final concentration 10γ/ml in 90 ml), which have been filtered under sterile conditions through a millipore filter (pore size:

$0.2\mu$) resulted in a suspension of $2 \times 10^7$ trypanosomes/ml. This suspension was incubated for 24 hours at 28° C in an incubator. After 24 hours, it was centrifuged again at 4500 r.p.m. at 4° C in the Sorvall centrifuge. The supernatent material was eliminated, and the sediment was taken up in 18 ml of medium.

The final concentration of $1 \times 10^8$ trypanosomes/ml obtained was, for example, suitable for immunizing mice.

What is claimed is:

1. A process for the manufacture of a substance having immunological activity, which comprises incubating trypanosomes that have been suspended in a monophase, aqueous, liquid culture medium with a phenanthridine derivative until they lose their pathogenicity, and then collecting the trypanosomes thus attenuated.

2. A process as claimed in claim 1, wherein the phenanthridine derivative used is 3,8-diamino-5-ethyl-6-phenyl-phenanthridinium bromide.

3. A process as claimed in claim 1, wherein the culture medium is free from proteins.

4. A process as claimed in claim 1, wherein the composition of trypanosomes in the suspension ranges from $10^3$ to $10^8$/ml.

5. A process as claimed in claim 1, wherein the phenanthridine derivative is used in a concentration of 0.5 to 1000$\gamma$/ml.

6. A process as claimed in claim 1, wherein incubation is carried out for 1 to 120 hours at 18° – 37° C.

7. A process as claimed in claim 1, wherein the concentration of trypanosomes in the suspension ranges from $1 \times 10^7$ to to $5 \times 10^7$/ml.

8. A process as claimed in claim 1, wherein the phenanthridine derivatives is used in a concentration of 5 to 100$\gamma$/ml.

9. A process as claimed in claim 1, wherein the incubation is carried out for 20 to 48 hours at 25°–33° C.

10. Chemically attenuated trypanosomes as obtained according to claim 1.

11. A vaccine effective against the Chagas disease, containing attenuated trypanosomes as claimed in claim 10 as the active ingredient.

* * * * *

UNITED STATES PATENT AND TRADEMARK OFFICE
CERTIFICATE OF CORRECTION

PATENT NO. : 4,024,242
DATED : May 17, 1977
INVENTOR(S) : Klaus-Dieter Hungerer

It is certified that error appears in the above-identified patent and that said Letters Patent are hereby corrected as shown below:

In the Heading, Item [73], replace "Hoechst Aktiengesellschaft" by --Behringwerke Aktiengesellschaft--.

Signed and Sealed this sixteenth Day of August 1977

[SEAL]

Attest:

RUTH C. MASON
Attesting Officer

C. MARSHALL DANN
Commissioner of Patents and Trademarks